United States Patent [19]

Sato et al.

[11] 4,115,310

[45] Sep. 19, 1978

[54] LIQUID CRYSTALLINE COMPOSITION

[75] Inventors: Hisato Sato, Tokyo; Masayuki Tazume, Urawa; Takasi Yamaki, Tokyo; Yutaka Fujita, Yokohama; Yoshi Arai, Oyama, all of Japan

[73] Assignees: Dainippon Ink & Chemicals Inc., Tokyo; Kawamura Institute of Chemical Research, both of Japan

[21] Appl. No.: 731,645

[22] Filed: Oct. 13, 1976

[30] Foreign Application Priority Data

Oct. 15, 1975 [JP] Japan ................. 50-124199

[51] Int. Cl.$^2$ ..................... C09K 3/34; G02F 1/13
[52] U.S. Cl. ..................... 252/299; 350/350
[58] Field of Search ............ 252/299, 408 LC; 350/160 LC

[56] References Cited

U.S. PATENT DOCUMENTS

| 3,888,566 | 6/1975 | Toriyama et al. | 252/299 |
| 3,922,067 | 11/1975 | Murao et al. | 252/299 |
| 3,956,168 | 5/1976 | Arai et al. | 252/299 |
| 3,963,638 | 6/1976 | Bucher et al. | 252/299 |
| 3,966,631 | 6/1976 | Toriyama et al. | 252/299 |

Primary Examiner—Benjamin R. Padgett
Assistant Examiner—T. S. Gron
Attorney, Agent, or Firm—Sherman & Shalloway

[57] ABSTRACT

A liquid crystalline composition comprising a nematic liquid crystalline substance and as an additive, a 1,8-diazo-bicyclo(5,4,0) undecene-7 alkyl ammonium salt of benzoic acid optionally having a substituent at the para position.

8 Claims, 8 Drawing Figures

LIQUID CRYSTALLINE COMPOSITION

This invention relates to a liquid crystalline composition suitable for use as a liquid crystal display element of a dynamic scattering mode (to be referred to as a DSM element).

As is well known, DSM elements utilize a strong light scattering phenomenon which occurs when an electric field having an intensity greater than a certain limit is applied to a nematic liquid crystalline substance. Specifically, when a liquid crystalline composition having negative dielectric anisotropy and resulting from the addition of an ionically conductive substance to a nematic liquid crystalline substance is interposed between electrodes, and an electric field having an intensity greater than a certain limit is applied to it, the liquid crystalline molecules are uniformly oriented at a certain angle to the direction of the electric field, and on the other hand, the ion migration occurring in the direction of the electric field causes the liquid crystalline molecules to rotate in the direction of the electric field. Consequently, an innumerable number of small areas having a different orientation from the surrounding are formed on the track of the ion that has migrated, and strong light scattering occurs on the interfaces of these areas. The DSM elements operate on the basis of this light scattering phenomenon.

In theory, therefore, no special restriction is imposed on the molecular orientation of the DSM elements in the absence of an electric field. But for practical purposes, the uniformity of molecular orientation is of greater importance. Non-uniformity in molecular orientation causes light scattering even in the absence of an electric field, and the DSM elements look cloudy with white. Thus, the light scattering intensity in the presence of an electric field decreases correspondingly to reduce the clarity of the image displayed. Attempts to obviate this defect have stimulated active research about the utilization of the uniform orientation of liquid crystalline molecules in DSM elements.

There are two methods for molecular orientation, one being a direct method in which the surface of a liquid crystal support plate is directly subjected to an orienting treatment, and the other being an indirect method in which an orienting agent is added to a nematic liquid crystalline substance. The present invention pertains to the indirect method.

Known orienting agents include, for example, tetraalkylammonium salts derived from simple inorganic acids such as hexadecyl trimethyl ammonium bromide disclosed in U.S. Pat. No. 3,656,834, polyamide resins such as VERSAMID-100 (a trademark for a product of General Mill Co.) disclosed in U.S. Pat. No. 3,803,503, and tetraalkyl ammonium salts of benzoic acid derivatives such as a tetraalkyl ammonium salt of p-butoxybenzoic acid disclosed in German OLS No. 2,209,127. These conventional orienting agents, however, are not entirely satisfactory with regard to the uniformity of molecular orientation.

It is an object of this invention therefore to provide a liquid crystalline composition suitable for use in DSM elements, as a result of finding an orienting agent free from such a defect.

The present inventors found that a liquid crystalline composition obtained by adding a 1,8diazo-bicyclo(5,4,0) undecene-7 alkyl ammonium salt of benzoic acid optionally having a substituent at the para-position to a nematic liquid crystalline substance can spontaneously form, in the absence of an electric field, a uniform orientation perpendicular to the wall surface, that is, an orientation whereby the long axes of the molecules are aligned perpendicular to the support plate, and has an electric resistivity suitable for dynamic scattering mode without the need to add an ionically conductive substance.

Thus, according to this invention, there is provided a liquid crystalline composition comprising a nematic liquid crystalline substance and as an additive, a 1,8-diazo-bicyclo (5,4,0) undecene-7 alkyl ammonium salt of benzoic acid optionally having a substituent at the para-position.

Compounds expressed by the following general formula

[I]

wherein X is an amino group, a nitro group, a chlorine atom, a hydrogen atom, or a straight-chain alkyl group containing 1 to 6 carbon atoms, and R is a straight-chain alkyl group containing 10 to 20 carbon atoms with the proviso that when X is a hydrogen atom or a straight-chain alkyl group containing 1 to 6 carbon atom, R is a straight-chain alkyl group containing 14 to 20 carbon atoms, are especially useful as the additive. The amount of such a compound is preferably 0.05 to 0.5% by weight, especially preferably 0.1 to 0.3% by weight, based on the weight of the nematic liquid crystalline substance.

The above additives work effectively on all nematic liquid crystalline substances having negative dielectric anisotropy. Such nematic liquid crystalline substances are, for example, benzylidene aniline-type nematic liquid crystalline substances of the general formula wherein $R_1$ and $R_2$ both represent $C_nH_{2n+1}-$, $C_nH_{2n+1}O-$, or $C_nH_{2n+1}COO-$, in which $n$ is an integer of 1 to 9, azoxybenzene-type nematic liquid crystalline substances of the general formula wherein $R_1$ is $C_nH_{2N+1}-$, or $C_nH_{2n+1}O-$, and $R_2$ is $C_nH_{2n+1}-$, $C_nH_{2n+1}O-$, or $C_nH_{2n+1}COO-$, in which $n$ is an integer of 1 to 9, phenyl benzoate-type nematic liquid crystalline substances of the general formula wherein $R_1$ is $C_nH_{2n+1}-$, or $C_nH_{2n+1}O-$, and $R_2$ is $C_nH_{2n+1}-$ or $C_nH_{2n+1}COO-$, in which $n$ is an integer of 1 to 9, and mixtures of these substances.

The 1,8-diazo-bicyclo(5,4,0) undecene-7 alkyl ammonium salts of benzoic acid or para-substituted benzoic acid may be produced by the following method.

Equimolar amounts of 1,8-diazo-bicyclo(5,4,0) undecene-7 and an alkyl bromide are reacted in isopropyl alcohol for 5 hours at 80° C, and the reaction product is precipitated, separated by filtration, washed, and recrystallized to afford a 1,8-diazo-bicyclo(5,4,0) undecene-7 alkyl bromide. Then, the product is reacted with a stoichiometrical amount of silver oxide in methanol at room temperature for 1 hour. The by-product silver bromide is separated by filtration to afford a methanol solution of a 1,8-diazo-bicyclo(5,4,0) undecene-7 alkyl hydroxide. To the methanol solution is added a stoichiometrical amount of benzoic acid or para-substituted benzoic acid. Methanol and water generated are distilled off at 100° C under high vacuum. The crude product obtained is washed, and recrystallized to afford the intended 1,8-diazo-bicyclo(5,4,0) undecene-7 alkyl ammonium salt of benzoic acid or para-substituted benzoic acid.

A first characteristic of the liquid crystalline composition of this invention is that an extremely uniform orientation perpendicular to the wall surface can be formed. When the liquid crystalline composition of this invention is filled in a liquid crystal cell, the liquid crystalline molecules are spontaneously oriented extremely uniformly with their long axes being in a direction at right angles to the support plate.

The ability of the liquid crystalline composition to be oriented perpendicularly to the wall surface is great when the content of the additive is at least 0.05% by weight. Irrespective of whether the wall surface of the support plate is made of a conductive layer such as tin oxide or indium oxide, or glass, the liquid crystalline molecules are almostly completely oriented perpendicular to the wall surface. Accordingly, DSM elements obtained by using the liquid crystalline composition of this invention do not cause light scattering resulting from non-uniform molecular orientation, and therefore, are completely transparent in the absence of an electric field. Furthermore, the liquid crystalline composition of this invention can retain its ability with uniform orientation at right angles to the wall surface even after it has been used for long periods of time. For example, even when an AC current of 60 Hz is continuously applied to a DSM element comprising the liquid crystalline composition of this invention for more than 10,000 hours, substantially no disturbance occurs in its molecular orientation, and it can still form a clear image display.

A second characteristic of the liquid crystalline composition of this invention is that without any special need to add another ionically conductive substance, it has an electric resistivity suitable for dynamic scattering mode. When the content of the additive in the liquid crystalline composition of this invention is 0.05 to 0.5% by weight based on the weight of the nematic liquid crystalline substance, it can form a uniform orientation perpendicular to the wall surface, and at the same time, its specific resistivity can be adjusted to $1 \times 10^7$ to $1 \times 10^{10}$ ohms-cm. In addition, the liquid crystalline composition of this invention whose specific resistivity is limited to the above range has an especially increased light scattering intensity at an impressing voltage of not more than 30 V. Because of this and the aforesaid ability to be oriented uniformly at right angles to the wall surface, the liquid crystalline composition of this invention can form a vivid display image when applied to DSM elements, and are therefore, especially suitable for practical applications.

The following Examples specifically illustrate the present invention. In these examples, the measurement of the ability with uniform orientation perpendicular to the wall surface (which will be referred to simply as "orientability"), the light transmission characteristics and specific resistivity was performed at a temperature of 25° C.

The accompanying drawings are for facilitating the understanding of the Examples.

EXAMPLE 1

A nematic liquid crystalline substance of the following formulation was prepared.

| Nematic liquid crystalline substance (A) | |
|---|---|
| p-Methoxybenzylidene-p'-butylaniline | 36 mole% |
| p-Ethoxybenzylidene-p'-butylaniline | 40 mole% |
| p-Butoxybenzylidene-p'-butylaniline | 24 mole% |
| (Nematic liquid crystal temperature range: −12 to 63° C.) | |

Two glass sheets each having on its surface a transparent electrode composed of a thin film of tin oxide were arranged parallel to each other with the transparent electrodes facing inwards, thereby to produce a cell with an interelectrode distance of 20 microns.

A liquid crystal composition prepared by adding 0.1% by weight, based on the nematic liquid crystalline substance (A), of 1,8-diazo-bicyclo(5,4,0) undecene-7 hexadecyl ammonium p-aminobenzoate to the nematic liquid crystalline substance (A) was filled in the resulting cell to form a liquid crystal cell (A-1) of the invention. As a comparison, the nematic liquid crystalline substance (A) containing no additive was filled in the cell to form a liquid cell (A-0). As further comparisons, liquid crystalline compositions prepared by adding 0.1% by weight, based on the liquid crystalline substance (A), of VERSAMID-100, hexadecyl trimethyl ammonium bromide, and tetrabutyl ammonium p-n-heptylbenzoate, respectively, to the nematic liquid crystalline substance (A) were filled in the cells to form liquid crystal cells (A-2), (A-3) and (A-4).

The orientability, the light transmission characteristics and the specific resistivity of the resulting liquid crystal cells were measured by the following methods.

Orientability

Figure 1:
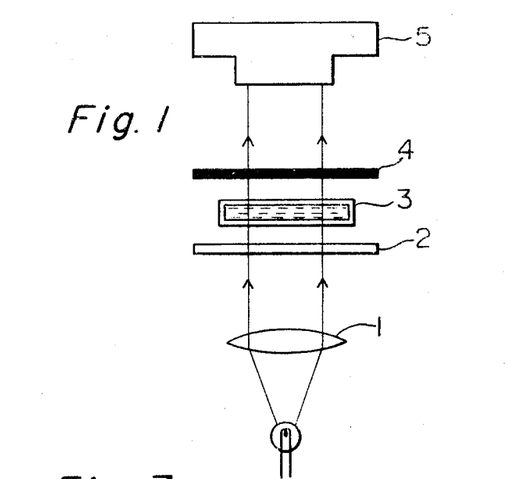
FIG. 1 shows an optical device for photographing the state of liquid crystalline molecules being oriented perpendicular to the wall surface in a liquid crystal cell.

As shown in FIG. 1, a light source, a lens 1, a polarizer 2, a liquid crystal cell 3, a photodetector 4, and a camera 5 are arranged sequentially. The polarizing surface of the polarizer is placed at right angles to the polarized surface of the photodetector, and the state of the liquid crystalline molecules in the liquid crystal cell being oriented perpendicular to the wall surface is photographed.

In the optical device shown in FIG. 1, light rays emitted from the light source are converted to parallel light rays by the lens, polarized by the polarizer, and transmitted through the liquid crystal cell which is under no electric field. If at this time, the liquid crystalline molecules in the liquid cell are oriented uniformly at right angles to the wall surface, the light rays do not undergo the rotation of the polarized surface, and therefore are completely shielded by the photodetector. As a result, a photograph with a uniformly dark image is obtained. However, when there are non-uniform areas in the orientation of the liquid crystalline molecules in a direction perpendicular to the wall surface, the light rays that pass through the non-uniform areas undergo the rotation of the polarized surface, and therefore, reach the camera without interception. Since the light rays which pass through the uniformly oriented region are shut off by the photodetector, there is obtained a photograph with bright non-uniformly oriented areas, and dark uniformly oriented areas.

Figure 2:
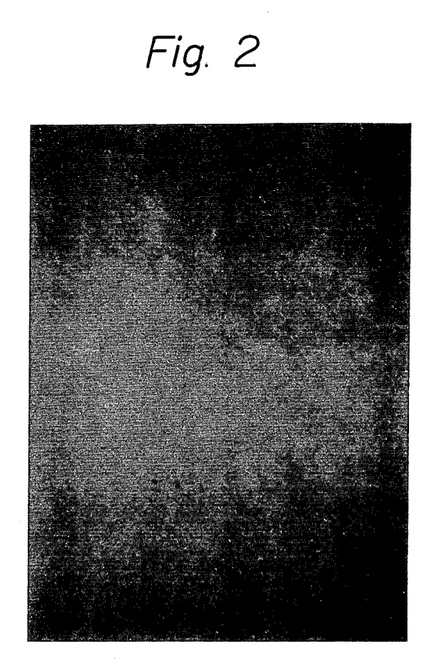
FIGS. 2 to 6 are photographs (5X) of the oriented states of liquid crystal cells produced in Example 1, FIG. 2 showing an example of the invention, and FIGS. 3 to 6 showing comparisons.
Figure 3:
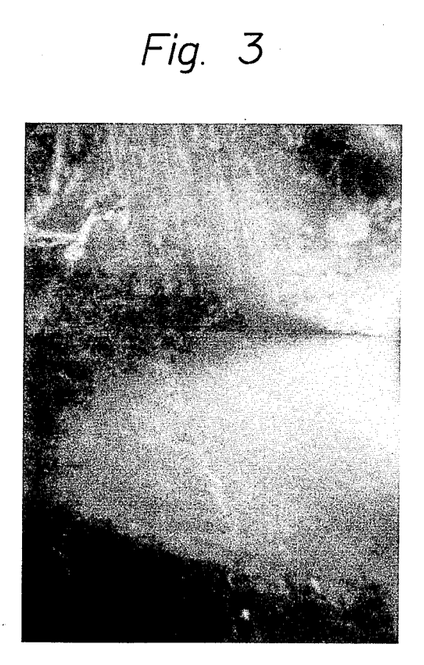
Figure 4:
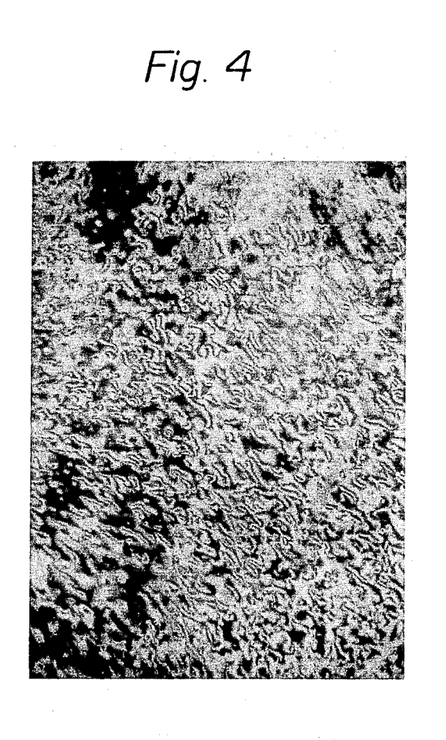
Figure 5:
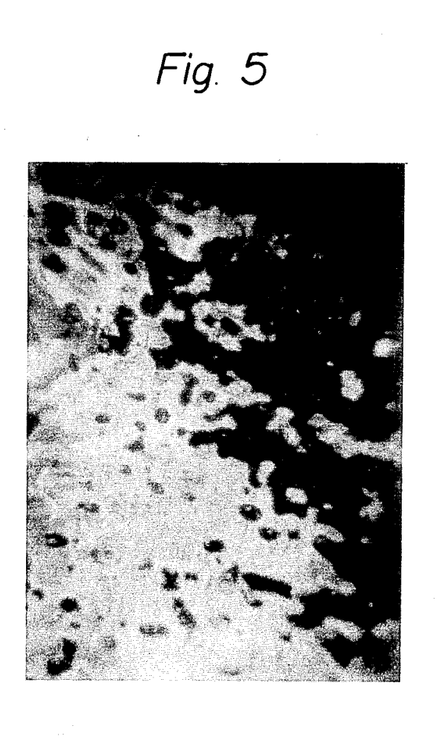
Figure 6:
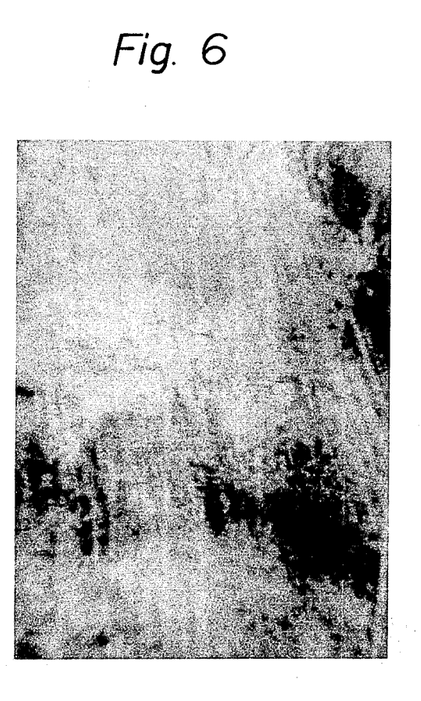

When the oriented states of the liquid crystalline molecules in each of the liquid crystal cells were photographed with a magnification of 5X, the photograph shown in FIG. 2 was obtained with the liquid cell (A-1) of the invention, and the photographs in FIGS. 3, 4, 5 and 6 were obtained with regard to the liquid crystal cells (A-0), (A-2), (A-3), and (A-4), respectively.

It can be seen from these photographs that the liquid crystal cell (A-1) of this invention is oriented at right angles to the wall surface more uniformly than any other liquid crystal cell in these comparisons.

Light Transmission Characteristics, and Specific Resistivity

Figure 7:
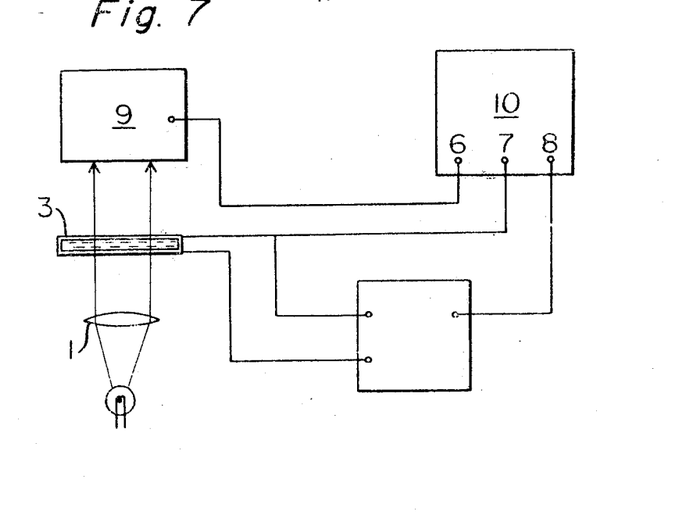
FIG. 7 shows a device for measuring the light transmission characteristics and specific resistivity of a liquid crystal cell.

The light transmission characteristic and specific resistivity were measured by the device shown in FIG. 7.

The light rays emitted by putting on a tungsten-filament lamp by means of a DC stabilized source are converted to parallel rays by a lens 1, and then pass through a liquid crystal cell 3. At this time, an AC voltage with 60 Hz is applied to the liquid crystal cell to vary the voltage continuously from 0 to 50 V. Changes in the intensity of light scattering caused by this are detected by means of a photoelectric amplifier 9 as changes in light transmittance. They are converted to electrical signals and recorded in an X-Y recorder 10. Thus, a light transmission characteristic curve shown in FIG. 8 is obtained.

The specific resistivity of the liquid crystal cell is determined from the electric current values separately recorded in the X-Y recorder. The specific resistivity values obtained are shown in Table 1. In FIG. 7, the reference numeral 6 represents a light transmitting terminal; 7, a current measuring terminal; and 8, a terminal for measuring the voltage applied.

Figure 8:
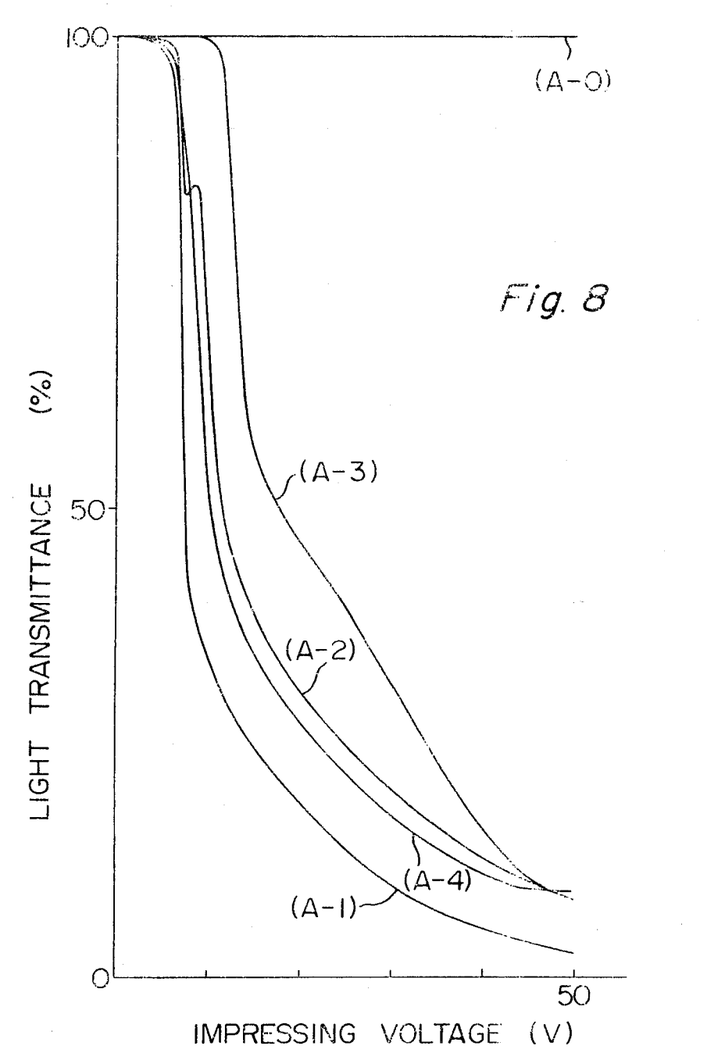
FIG. 8 is a graphic representation showing the light transmission characteristics of liquid crystal cells produced in Example 1.

It can be understood from FIG. 8 that the liquid crystal cell (A-1) of this invention has a greater light scattering intensity than the comparative liquid crystal cells (A-0), (A-2), (A-3), and (A-4) at an impressing voltage of not more than 30 V.

Table 1

| Liquid crystal cell | Additive | Specific resistivity (ohms-cm) |
| --- | --- | --- |
| A-1 | [1,8-Diazo-bicyclo(5,4,0) undecene-7 hexadecyl ammonium p-aminobenzoate structure] | $4 \times 10^8$ |
| A-0 | — | $5 \times 10^{10}$ |
| A-2 | VERSAMID-100 | $9 \times 10^9$ |
| A-3 | $n\text{-}C_{16}H_{33}\overset{\oplus}{N}(CH_3)_3 \cdot \overset{\ominus}{Br}$ | $1 \times 10^{10}$ |
| A-4 | $(n\text{-}C_4H_9)_4\overset{\oplus}{N} \cdot \overset{\ominus}{OOC}\text{-}\bigcirc\text{-}n\text{-}C_7H_{15}$ | $4 \times 10^8$ |

EXAMPLE 2

1,8-Diazo-bicyclo(5,4,0) undecene-7 hexadecyl ammonium salts of benzoic acid derivatives of the following general formula

[Structural formula: bicyclic amidinium-N—n-C$_{16}$H$_{33}$ · $^{\ominus}$OOC—⟨benzene ring⟩—X]

wherein —X is as shown in Column I of Table 2 were used as additives. Various liquid crystal compositions were prepared by adding 0.3% by weight of these additives to the nematic liquid crystalline substance (A), and each of them was filled in the cell produced in Example 1. All of these liquid crystal cells showed almost the same orientability and light transmission characteristics as the liquid crystal cell (A-1) in Example 1. The specific resistivities of these liquid crystal cells were as shown in Column II of Table 2.

Table 2

| Run No. | I —X of the additive | II Specific resistivity (ohms-cm) |
| --- | --- | --- |
| 1 | —NH$_2$ | $1.7 \times 10^8$ |
| 2 | —NO$_2$ | $8.3 \times 10^7$ |
| 3 | —Cl | $8.4 \times 10^7$ |
| 4 | —H | $8.6 \times 10^7$ |
| 5 | —CH$_3$ | $9.0 \times 10^7$ |
| 6 | —n-C$_3$H$_7$ | $1.0 \times 10^8$ |
| 7 | —n-C$_4$H$_9$ | $1.1 \times 10^8$ |
| 8 | —n-C$_6$H$_{13}$ | $1.4 \times 10^8$ |

EXAMPLE 3

1,8-Diazo-bicyclo(5,4,0) undecene-7 dodecyl ammonium salts of benzoic acid derivatives of the general formula wherein —X is as shown in Column I of Table 3 were used as additives. These additives were added in an amount of 0.1 or 0.3% by weight to the nematic liquid crystalline substance (A) to form various liquid crystalline compositions, which were each filled in the cell produced in Example 1. All of the resulting liquid crystal cells had almost the same orientability and light transmission characteristics as the liquid crystal cell (A-1). The specific resistivities of these liquid crystal cells were as shown in Column III of Table 3.

Table 3

| Run No. | I<br>—X of the additive | II<br>Amount (% by weight) | III<br>Specific resistivities (ohms-cm) |
| --- | --- | --- | --- |
| 1 | —NH$_2$ | 0.1 | 3.5 × 10$^8$ |
|   |        | 0.3 | 1.4 × 10$^8$ |
| 2 | —NO$_2$ | 0.1 | 2.2 × 10$^8$ |
|   |        | 0.3 | 7.8 × 10$^7$ |
| 3 | —Cl    | 0.1 | 2.4 × 10$^8$ |
|   |        | 0.3 | 7.9 × 10$^7$ |

EXAMPLE 4

A nematic liquid crystalline substance of the following formulation was prepared.

| Nematic liquid crystalline substance (B) | |
| --- | --- |
| p-Methoxybenzylidene-p'-n-propylaniline | 25 mole% |
| p-Ethoxybenzylidene-p'-n-propylaniline | 25 mole% |
| p-Methoxybenzylidene-p'-n-hexylaniline | 25 mole% |
| p-Ethoxybenzylidene-p'-n-hexylaniline | 25 mole% |

( Nematic liquid crystal temperature range: −32 to 67° C.
  Specific resistivity: 5 × 10$^{10}$ ohms-cm )

1,8-diazo-bicyclo(5,4,0) undecene-7 tetradecyl ammonium salts of benzoic acid derivatives of the general formula wherein —X is as shown in Column I of Table 4 were used as additives, and added to the nematic liquid crystalline substance (B) in an amount of 0.3% by weight to form various liquid crystalline compositions, which were each filled in the cell of Example 1. All of the liquid crystal cells showed almost the same orientability and light transmission characteristics as the liquid crystal cell (A-1). The specific resistivities of these crystal cells were as shown in Column II of Table 4.

Table 4

| Run No. | I<br>—X of the additive | II<br>Specific resistivity (ohms-cm) |
| --- | --- | --- |
| 1 | —NH$_2$ | 1.5 × 10$^8$ |
| 2 | —NO$_2$ | 8.0 × 10$^7$ |
| 3 | —Cl | 8.1 × 10$^7$ |
| 4 | —H | 8.2 × 10$^7$ |
| 5 | —CH$_3$ | 8.4 × 10$^7$ |
| 6 | —n-C$_3$H$_7$ | 9.5 × 10$^7$ |
| 7 | —n-C$_4$H$_9$ | 9.8 × 10$^7$ |
| 8 | —n-C$_6$H$_{13}$ | 1.2 × 10$^8$ |

EXAMPLE 5

1,8-Diazo-bicyclo(5,4,0) undecene-7 octadecyl ammonium salts of benzoic acid derivatives of the general formula wherein —X is as shown in Column I of Table 5 were used as additives, and added to the nematic liquid crystalline substance (B) used in Example 4 in an amount of 0.1% by weight to form various liquid crystalline compositions, which were each filled in the cell produced in Example 1. All of the resulting cells showed much the same orientability and light transmission characteristics as the liquid crystal cell (A-1) in Example 1. The specific resistivities of these crystal cells were as shown in Column II of Table 5.

Table 5

| Run No. | I<br>—X of the additive | II<br>Specific resistivity (ohms-cm) |
| --- | --- | --- |
| 1 | —NH$_2$ | 5.2 × 10$^8$ |
| 2 | —NO$_2$ | 2.9 × 10$^8$ |
| 3 | —Cl | 2.9 × 10$^8$ |
| 4 | —H | 2.3 × 10$^8$ |
| 5 | —CH$_3$ | 3.1 × 10$^8$ |
| 6 | —n-C$_3$H$_7$ | 3.3 × 10$^8$ |
| 7 | —n-C$_4$H$_9$ | 3.9 × 10$^8$ |
| 8 | —n-C$_6$H$_{13}$ | 5.8 × 10$^8$ |

EXAMPLE 6

1,8-Diazo-bicyclo(5,4,0) undecene-7 decyl ammonium salts of benzoic acid derivatives of the general formula in which —X is —NH$_2$, —NO$_2$ or —Cl were added in an amount of 0.3% by weight to a nematic liquid crystalline substance composed of 50 mole% of p-methoxybenzylidene-p'-n-butylaniline, 33 mole% of p-methoxybenzylidene-p'-n-butanoyloxyaniline and 17 mole% of p-ethoxyphenyl-p'-n-caproylbenzoate to form various liquid crystalline compositions, which were each filled in the cell produced in Example 1. All of the resulting liquid crystal cells showed uniform orientation perpendicular to the wall surface.

EXAMPLE 7

1,8-Diazo-bicyclo(5,4,0) undecene-7 eicosyl ammonium salts of benzoic acid derivatives of the general formula wherein —X is —NH$_2$, —NO$_2$, —n—C$_3$H$_7$ or —n—C$_6$H$_{13}$ were added in an amount of 0.3% by weight to a nematic liquid crystalline substance composed of 50 mole% of p-methoxy-p'-ethylazoxybenzene and 50 mole% of p-methoxy-p'-butylazoxybenzene to form various liquid crystalline compositions, which were each filled in the cell produced in Example 1. All of these liquid crystal cells showed uniform orientation perpendicular to the wall surface.

What we claim is:

1. A liquid crystalline composition comprising a nematic liquid crystalline substance having negative dielectric anisotropy and as an additive, at least one compound of the general formula wherein X is an amino group, a nitro group, a chlorine atom, a hydrogen atom, or a straight-chain alkyl group containing 1 to 6 carbon atoms, and R is a straight-chain alkyl group containing 10 to 20 carbon atoms with the proviso that when X is a hydrogen atom or a straight-chain alkyl group containing 1 to 6 carbon atoms, R is a straight-chain alkyl group containing 14 to 20 carbon atoms, and said additive being used in the range of 0.05 to 0.5% by weight of the nematic liquid crystalline substance.

2. The liquid crystalline composition according to claim 1 wherein X is an amino group.

3. The liquid crystalline composition according to claim 1 wherein X is a nitro group.

4. The liquid crystalline composition according to claim 1 wherein X is a chlorine atom.

5. The liquid crystalline composition of claim 1 wherein X is a hydrogen atom.

6. The liquid crystalline composition of claim 1 wherein X is a straight-chain alkyl group containing 1 to 6 carbon atoms.

7. The liquid crystalline composition according to claim 1 wherein said additive is used in an amount of 0.1 to 0.3% by weight, based on the weight of the nematic liquid crystalline substance.

8. The liquid crystalline composition according to claim 1 wherein the nematic liquid crystalline substance is selected from the group consisting of benzylidene aniline-type nematic liquid crystalline substances of the general formula wherein R$_1$ and R$_2$ both represent C$_n$H$_{2n+1}$—, C$_n$H$_{2n+1}$O—, or C$_n$H$_{2n+1}$COO—, in which n is an integer of 1 to 9, azoxybenzene-type nematic liquid crystalline substances of the general formula wherein R$_1$ is C$_n$H$_{2N+1}$—, or C$_n$H$_{2n+1}$O—, and R$_2$ is C$_n$H$_{2n+1}$—, C$_n$H$_{2n+1}$COO—, in which n is an integer of 1 to 9, and phenyl benzoate-type nematic liquid crystalline substances of the general formula wherein R$_1$ is C$_n$H$_{2n+1}$—, or C$_n$H$_{2n+1}$O—, and R$_2$ is C$_n$H$_{2n+1}$— or C$_n$H$_{2n+1}$COO—, in which n is an integer of 1 to 9, or mixtures of these substances.

* * * * *

UNITED STATES PATENT AND TRADEMARK OFFICE
CERTIFICATE OF CORRECTION

PATENT NO. : 4,115,310
DATED : September 19, 1978
INVENTOR(S) : Hisato Sato et al.

It is certified that error appears in the above—identified patent and that said Letters Patent are hereby corrected as shown below:

Claim 8, line 40, after $C_nH_{2n+1}-$, insert -- $C_nH_{2n+1}O-$, --

Signed and Sealed this

Ninth Day of January 1979

[SEAL]

Attest:

RUTH C. MASON
Attesting Officer

DONALD W. BANNER
Commissioner of Patents and Trademarks